United States Patent [19]

Eggleton et al.

[11] Patent Number: 4,546,771
[45] Date of Patent: Oct. 15, 1985

[54] ACOUSTIC MICROSCOPE

[75] Inventors: Reginald C. Eggleton; Francis J. Fry, both of Indianapolis, Ind.

[73] Assignee: Indianapolis Center for Advanced Research, Inc. (ICFAR), Indianapolis, Ind.

[21] Appl. No.: 531,917

[22] Filed: Sep. 14, 1983

Related U.S. Application Data

[63] Continuation-in-part of Ser. No. 354,708, Mar. 4, 1982, abandoned, which is a continuation-in-part of Ser. No. 114,705, Jan. 23, 1980, abandoned.

[51] Int. Cl.$^4$ ............................................. A61B 10/00
[52] U.S. Cl. ................................................... 128/660
[58] Field of Search ................................ 128/660–663, 128/24 A, 214 R; 73/618–626; 358/98, 112

[56] References Cited

U.S. PATENT DOCUMENTS

| 3,024,644 | 3/1962 | Fry et al. ........................ 128/660 X |
| 3,942,530 | 3/1976 | Northeved ........................ 128/4 X |
| 4,207,901 | 6/1980 | Nigam .............................. 128/660 |

FOREIGN PATENT DOCUMENTS 387698  9/1973  U.S.S.R. ............................. 128/660

Primary Examiner—Kyle L. Howell
Assistant Examiner—Francis J. Jaworski
Attorney, Agent, or Firm—Woodard, Weikart, Emhardt & Naughton

[57] ABSTRACT

The present invention relates to an ultrasound visualization system which has a capability of microscopic examination of tissue within the body without the need for removal of the tissue. A transducer, capable of producing and receiving high frequency acoustical beams is positioned within a needle. The acoustical beams are directed radially from the needle and are focused on a point which is outside of the needle and in the tissue. The microscope can be operated in either the pulse echo or pulse reflection mode. The needle can be inserted into a patient, and the acoustical beams are scanned to produce highly magnified images of cellular features of internal tissue or features of tissue architecture and structure helpful to the determination of tissue pathology.

20 Claims, 8 Drawing Figures

ACOUSTIC MICROSCOPE

CROSS REFERENCE TO RELATED APPLICATION

This application is a continuation-in-part of application Ser. No. 354,708 filed Mar. 4, 1982 which is a C-I-P of Ser. No. 114,705, filed Jan. 23, 1980, both now abandoned.

BACKGROUND OF THE INVENTION

1. Field of the Invention

The field of the invention relates to high resolution ultrasound visualization systems, particularly such systems which have applications in the field of medicine.

2. Brief Description of the Prior Art

In recent years ultrasound technology has become a valuable tool to medicine. Both x-rays and ultrasound waves are useful for visualization of internal structure in patients, however ultrasound waves possess many advantages over x-rays. Ultrasound waves in the low dosages used for visualization are relatively innocuous to the health of the patient, whereas x-ray radiation presents an acknowledged risk of tissue damage. Also certain types of soft tissue can be better differentiated by ultrasound waves than with x-rays. Particularly, tumors can often be detected without difficulty by an ultrasound visualization system.

Most ultrasound visualization systems operate externally, with a transducer being placed on the surface of the patient, or in proximity to the patient in an acoustical coupling medium. The internal structure of a patient can be detected either by the detection of reflection echoes or by through-transmission technology.

Some ultrasound systems have been adapted to be used within the body. See U.S. Pat. No. 3,938,502 to Bom, U.S. Pat. No. 3,817,089 to Eggleton et al., and German Offenlagungsschrift No. 2,305,501. By these systems, transducers are placed on catheters and can thus be positioned within hollow organs in the body. In this manner the internal structure of various organs, such as blood vessels or the heart, can be viewed ultrasonically. Such systems typically operate at a frequency in the range of 5 MHz to 15 MHz.

Another ultrasonic aid in medicine is the acoustic microscope, in which high frequency ultrasound radiation is focused on a subject to produce high resolution magnification. See "Acoustic Imaging with Holograph and Lenses" by Glenn Wade, *IEEE Transactions on Sonics and Ultrasonics,* Vol. SU22, No. 6, November, 1975, which discloses one such acoustic microscope which operates at a frequency of 600 MHz. While perhaps not prior art, see also "The Acoustic Microscope" by Calvin F. Quate, *Scientific American,* Vol. 241, No. 4, October, 1979.

Ultrasound visualization systems have also been used to guide manual operations within the interior of the human body. U.S. Pat. No. 4,029,084 to Soldner and U.S. Pat. No. 3,556,079 to Omizo are two such patents which disclose ultrasound systems which are used as an aid in guiding the medical instrument into the body, such as a needle to be used for the puncturing of a blood vessel.

SUMMARY OF THE INVENTION

In general terms, the present invention provides a high resolution ultrasound visualization system which has a capability of microscopic examination of tissue within the body without the need for removal of the tissue. This is particularly important in cases where the tissue involved is vital and not regenerative and therefore should only be removed if it is diseased. Implementation of this invention will permit the elimination of protracted and costly procedures presently used to determine tissue status. These procedures normally have involved the biopsic removal of tissue with subsequent tissue processing of slicing, fixing, mounting, staining and microscopic examination.

A transducer, capable of producing and receiving high frequency acoustical beams is positioned within a needle no larger than that presently acceptable for standard biopsy procedures in medical diagnostic practice. The acoustical beams are directed radially from the needle and are focused on a point which is outside of the needle. The needle can be inserted into a patient, and either mechanically or electronically scanned, or both, to produce highly magnified images of cellular features of internal tissue.

DESCRIPTION OF THE PREFERRED EMBODIMENT

Figure 1:
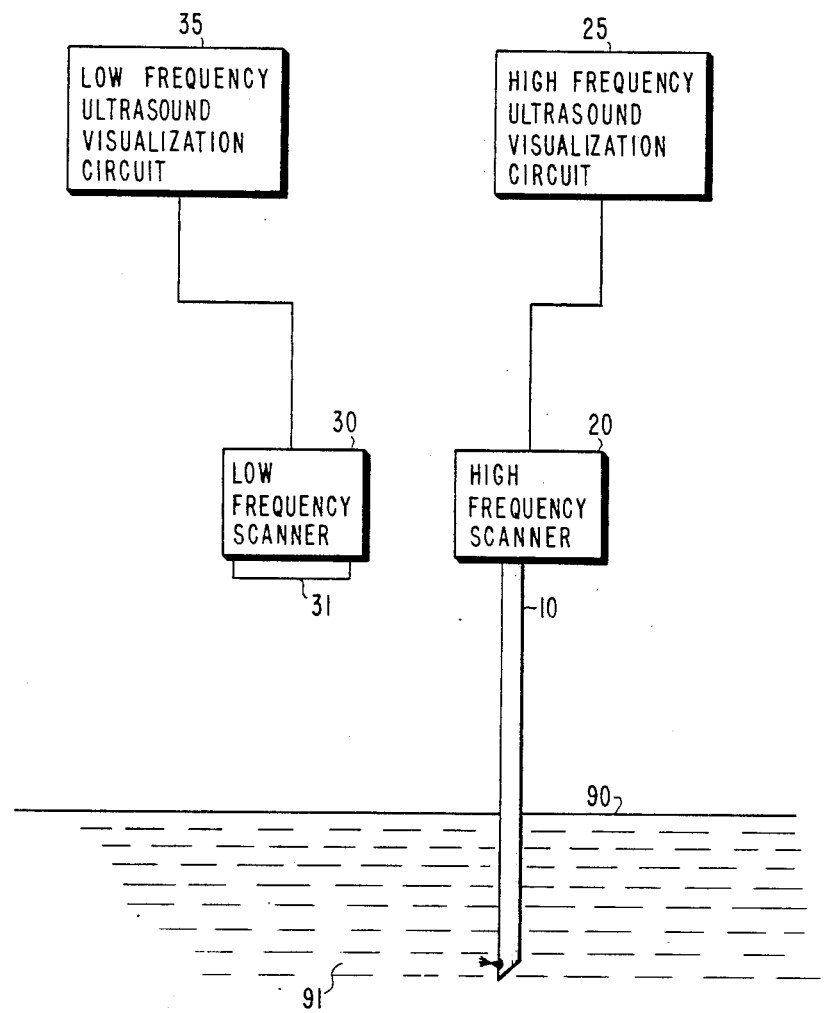
FIG. 1 is a schematic view of the ultrasound visualization system of the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 2:
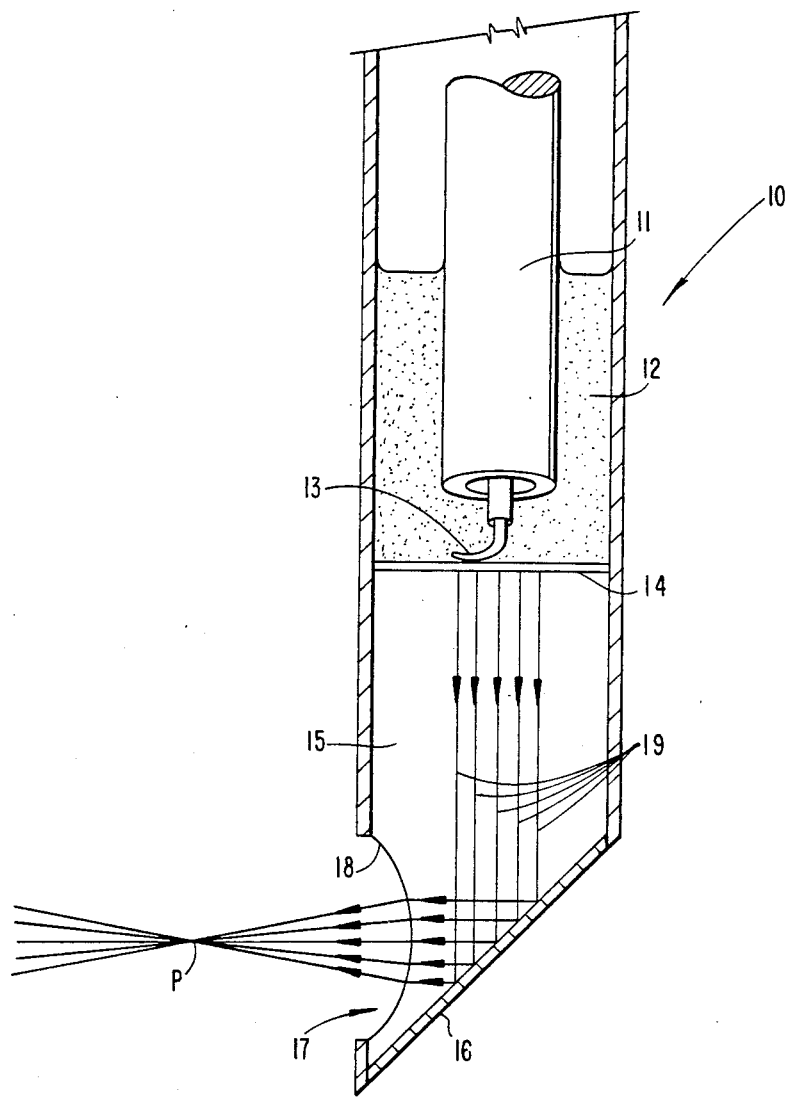
FIG. 2 is an enlarged, partial fragmentary view of the needle of FIG. 1.

Referring now to the drawings, particularly FIG. 2, needle 10 is tubular and has within it coaxial cable 11. Wire 13 of coaxial cable 11 connects with piezoelectric transducer 14 which is capable of generating and receiving acoustical beams up to of at least 500 MHz. High frequencies of 500 MHz or greater provide the resolution that is required to examine cellular features, although frequencies of the order of 100 MHz to 400 MHz do provide sufficient resolution to examine certain tissue architecture and organization which is useful for many pathological determinations. 400 MHz provides about 100×magnification and is suitable for about 90% of the applications. 100 MHz (about 25×magnification) provides sufficient magnification for some applications and can still be sized within a standard biopsy needle (no larger than 2 mm. in diameter). However, frequencies less than about 100 MHz (1) would not provide satisfactory magnification and (2) would require elements which are too large to fit within a standard biopsy needle.

The use of such high frequencies is required in the present invention because the wavelength of the sound must be short in comparison to the size of a cell in order to obtain satisfactory resolution. But it is also the use of these high frequencies which allows the transducer and coupling elements to be downsized in a straightforward manner to fit within a biopsy needle. Other ultrasound apparatus, operating in lower frequencies, would not fit within a biopsy needle of any acceptable size because of the longer wavelengths involved. On the other hand, elements used in the present invention are readily available in the size appropriate to fit within a biopsy needle since they need to be of such size to generate and focus ultrasound signals of such short wavelengths and are therfore well known to those skilled in this art.

Coupling medium 15 is sapphire, and is positioned within needle 10 in contact with transducer 14. Sapphire is selected in the preferred embodiment because of its high index of refraction and its comparatively low attenuation at high ultrasound frequencies. Other materials with similar properties may also be used as the coupling medium. Transducer 14 is standardly manufactured by an epitaxial process as is well known to those skilled in the art.

Acoustical beams 19 produced by transducer 14 travel axially within needle 10 until they are reflected by reflective surface 16, which is acoustically reflective in the range of frequencies used and is positioned within needle 10 in contact with coupling medium 15 at approximately a 45° angle to the central axis of needle 10. Reflection of acoustic beams 19 by reflective surface 16 directs acoustic beams 19 radially towards aperture 17 of needle 10. Spherical lens surface 18 of coupling medium 15 is shaped to focus acoustic beams 19 at a point P outside of needle 10. Depending upon the particular acoustical properties of the tissue at point P, various proportions of pulsed acoustical beams 19 are reflected back towards transducer 14 along the same path which acoustic beams 19 followed from transducer 14. These reflection echoes are received by transducer 14 and are translated into electrical impulses in wire 13.

By aiming acoustical beams 19 at a matrix of points and by testing for reflection echoes at these points, an acoustic image can be formed by high frequency visualization circuit 25. The magnification of the acoustic image may be chosen by appropriately selecting the distance between the points tested and the distance between these points as they are represented in the acoustic image. A limiting factor of the magnification is the resolution obtainable by the focused acoustic beams. This resolution can be increased by increasing the frequency (shortening the wave length) of the ultrasound waves.

Scanning may be accomplished either electronically, or by mechanical means, or by both. An example of electronic scanning would be the reception of acoustical reflections from various points near the actual focal point P differentiated by the time delay at which the echo pulses are sensed. By mechanical scanning, transducer 14 and sapphire coupling medium 15 are physically moved within needle 10, either axially (FIG. 5) or rotationally (FIGS. 4A and B), or both, to vary the position of the focal points at which the acoustical beams are directed. By combining scanning in two dimensions, a two dimensional picture can be obtained. Scanner 20 is used to effect the scanning desired while high frequency ultrasound visualization circuit 25 provides the two dimension images.

Two examples of suitable methods of scanning are the "B" mode scan and the "C" mode scan. By the "B" mode scan, one dimension is obtained by electronically scanning a range of distances from the needle, while the second dimension is provided by mechanical in either an axial or rotational direction within a stationary needle sleeve, or by electronic scanning. In a "C" mode scan, mechanical scanning (both axial and rotational) provides a two dimensional view at a specific distance (approximately at the focal depth) from needle 10. Scanning (either mechanical or electronic) determines the coordinates in the fixed depth surface being viewed. This distance or fixed depth may be adjusted by varying the time delay at which the echo pulses are sensed after they are transmitted.

In the case of an electronic phased array scan (FIG. 6) there is no relative motion between the array and the tissue since needle 10 is stationary and therefore there is no possibility of any undesirable motion effect induced in the tissue. As to mechanical scanning, the actual scanning is so rapid that physiologically induced tissue motion will no blur the image. To minimize whatever such induced motion that may occur however, the concavity of sapphire lens may be filled with material 120, 220, and 420 having tissue-like acoustical properties (plastisol) so that the external contour is similar to the shape of needle 10. Plastisol adhers to surface 18 by itself without the need for an adhesive. This material may not be needed though where body fluids fill the lens cavity permitting the lens to move in this liquid without moving adjacent tissue.

It may be desired for an operator to adjust the position of a visualized cell in the field of focus. This may be accomplished by injecting a fluid having low acoustical loss properties through needle 10 into the area near the lens (path not shown in drawings). By adjusting the pressure under which the fluid is injected the distance between the lens and the tissue can be correspondingly adjusted.

FIG. 1 is an overall schematic illustration of the preferred embodiment. A conventional low frequency transducer 31 (approximately 5 MHz) is mounted on a conventional low frequency system scanner 30, and is connected to a conventional low frequency ultrasound visualization circuit 35. Needle 10 is mounted to high frequency system scanner 20. Transducer 14 is connected to high frequency ultrasound visualization circuit 25 through wire 13 (the connection is not specifically shown).

In operation, low frequency scanner 30 (having a large field of view) may be either adjacent to skin surface 90 or immersed within a suitable liquid coupling medium 80. The low frequency ultrasound system, including visualization circuit 35, scanner 30 and transducer 31, are used to locate suspected tissue to be examined, such as a tumor. After the suspected tissue has been located by the low frequency ultrasound system, the high frequency ultrasound system, including high frequency visualization circuit 25, high frequency system scanner 20 and needle 10, are then used for a high magnification examination of the suspected tissue in situ. This is accomplished by inserting needle 10 into the patient and positioning the needle within the suspected tissue under the guidance of the low frequency ultrasound system. Alternatively, the suspected tissue may be located by fixedly mounting needle 10 and high frequency system scanner 20 to low frequency system scanner 30. Thus, when low frequency system locates the suspected tissue, the two scanners may be jointly moved the appropriate distance separating the low frequency transducer from needle 10, to place needle 10 in the proper position for an examination.

Figure 3:
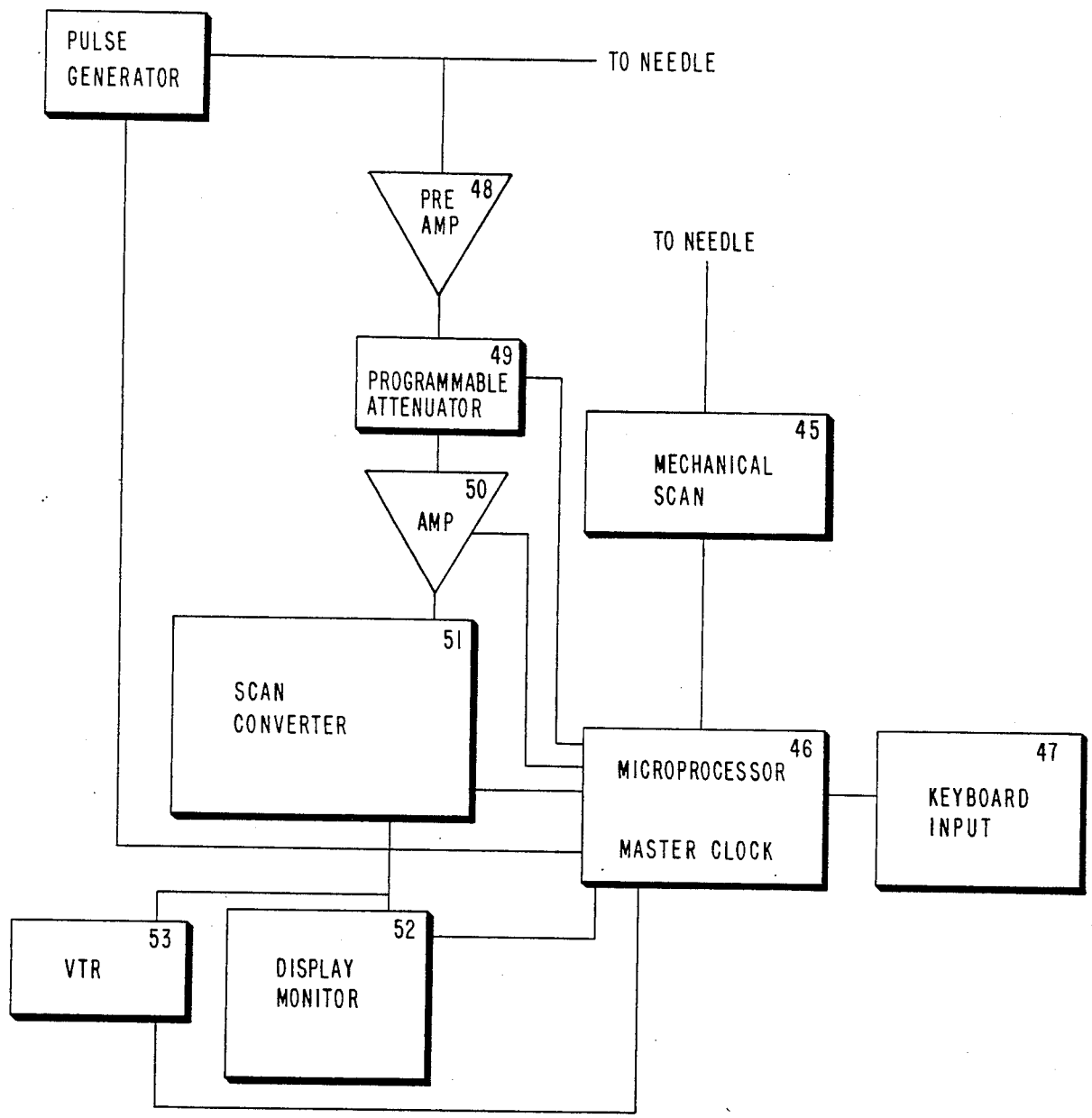
FIG. 3 is a block diagram showing electrnic system elements which operate to control the scanning system of the present invention.

FIG. 3 shows a block diagram of scanning control and visualization elements operating in conjunction with the ultrasound microscope needle, in order to obtain an appropriate image of human body tissue in situ. The entire system is under control of microprocessor 46 which accepts commands from keyboard 47. Mechanical scan system 45 rotates beam 60 by rotating saphire lens 15 and attached transducer element 14. Mechanical scan system 45 also indexes the spatial position of beam 60 to provide appropriate registration on scan converter 51 and on to display 22. Pulse generator 54 under control of microprocessor control 46 provides the appropriate pulse frequency to transducer 14 as well as the appropriate pulse shape. Returned acoustic signals from tissue are captured on the lens transmitted through 15 to transducer 14 and appropriately simplified by pre amp 48. Programmable attenuator 49 provides an appropriate signal level interface to amplifier 50 which feeds signals to scan converter 51 in appropriate spatial registry. Amplifier 50 has program selectable transfer function characteristics to aid in emphasizing various tissue characteristics.

Images on the tissue are provided on TV type display monitor 52 and also stored in video format on video tape recorder 53. Appropriate signal processing is provided in the output side of the scan converter to enhance tissue presentation. This signal processing is under selectable control through microprocessor 46.

Figure 4B:
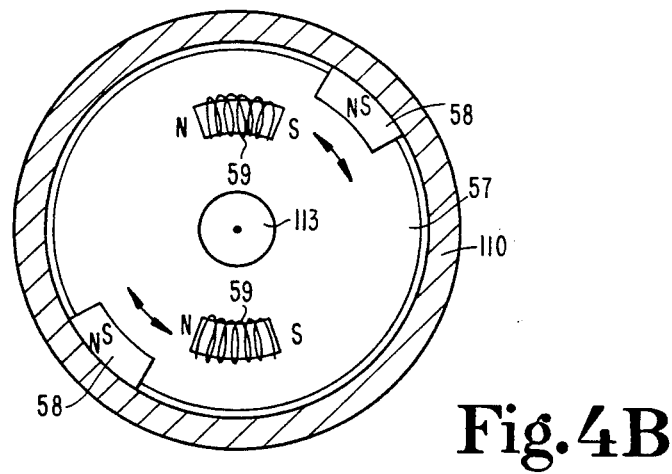
FIGS. 4A and 4B show a needle arrangement for obtaining a sector scan (arcical) of the observed tissue.
Figure 4A:
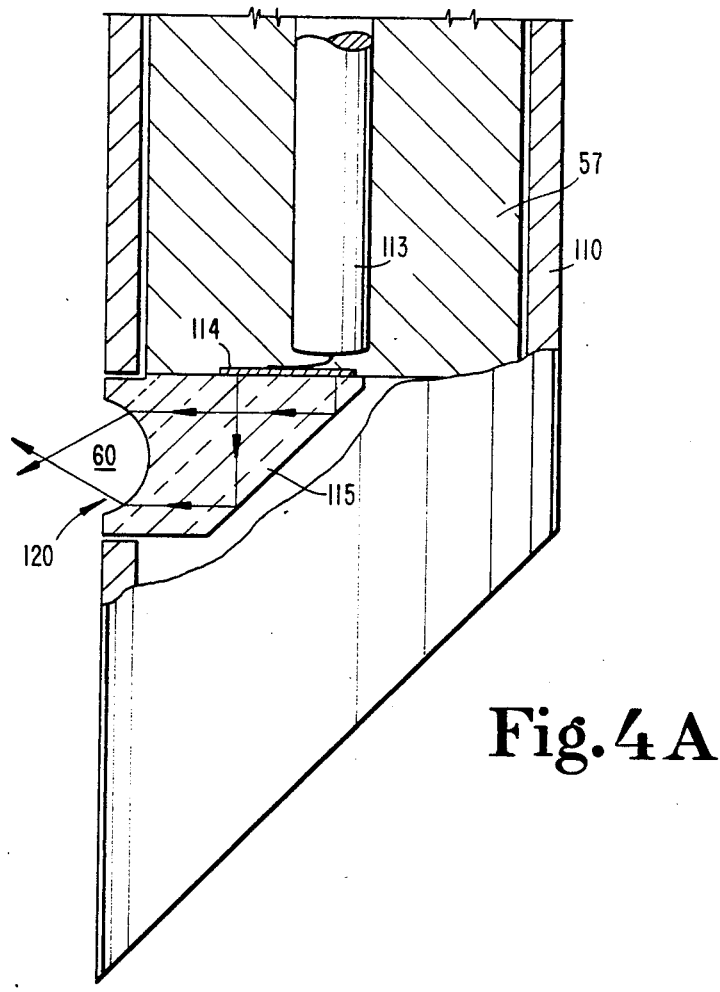

FIGS. 4A and 4B show one embodiment which generates a mechanical sector scan for sound beam 60. In this case the scan is accomplished by a rotary motion about the axis of the needle. Coupling sapphire 115 with attached transducer 114 is supported by rotating member 57. Rotating member 57 has attached small electromagnets 59 arcically polarized as shown. Permanent magnets 58 attached to needle 110 are polarized as shown. By oscillating the polarization of electromagnets 59, alternating attraction and repulsion with respect to permanent magnets 58 is created to cause rotating member 57 to arcically oscilate within needle 110, thereby providing a small sector scan. Coaxial cable 113 with center wire loop attaches to transducer 114 permitting a simple sector rotation for a mechanical scanning of the tissue being observed.

Figure 5:
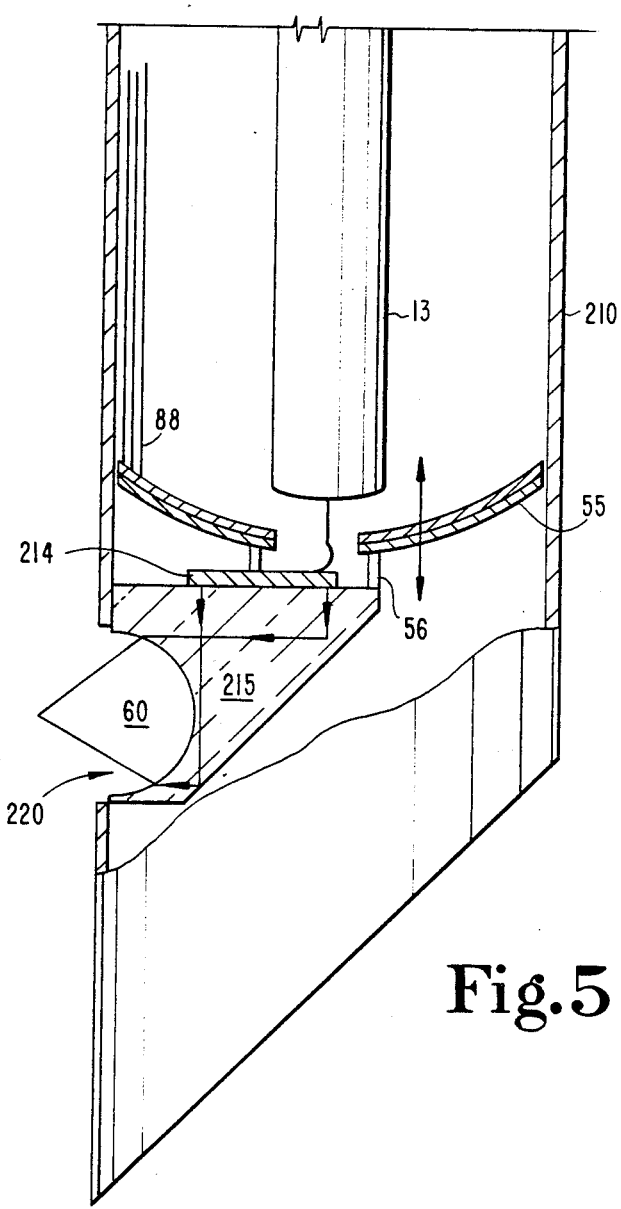
FIG. 5 shows another needle arrangement for obtaining a linear scan (axial) of the observed tissue.

FIG. 5 shows an embodiment of a mechanical linear scan along the needle 210 axis. Piezoelectric bimorph element 55 is flexed by electric drive (not shown) through lines 88 to produce an axial oscilatory motion. Bimorph element 55 is attached to needle housing 10 about its circumference. Element 56 attaches bimorph 55 to sapphire 215, thereby coupling sapphire 215 to the oscilatory motion of bimorph element 55 to generate a mechanical axial scan.

Figure 6:
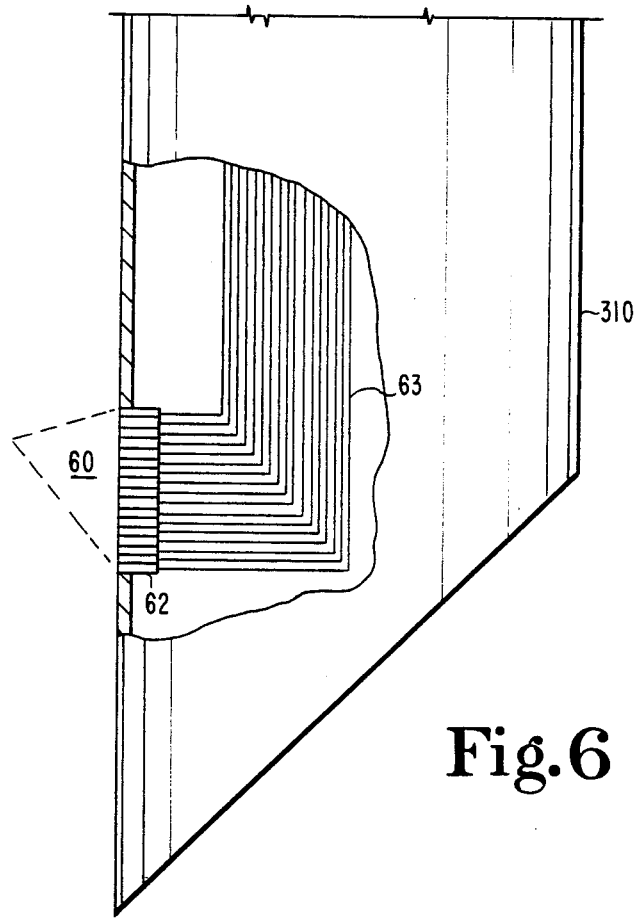
FIG. 6 illustrates a linear electronic scan with a linear phased array.

FIG. 6 shows a phased microarray 62 mounted in needle 310. Small photoetched wires 63 on appropriate substrate connect to individual elements of 62. This same substrate also supports elements of 62. Electronic steering and focusing are used to move beam 60 in the appropriate axial direction. Pulse excitation in appropriate time sequence provides for beam steering and focusing. Each element of 62 sequentially emits an acoustic wave excitation which combines in space to provide focusing and steering of the trasmit acoustic pulse. Beam steering and focusing are through use of phased microarray 62 are well know to those skilled in this particular art and therefore will not be further discussed.

Figure 7:
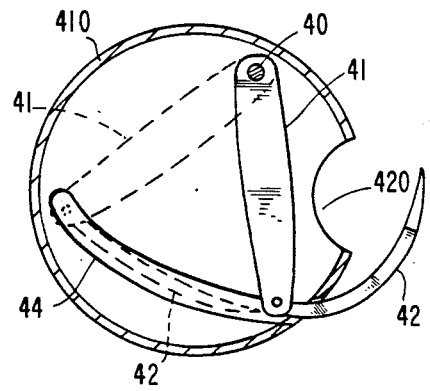
FIG. 7 shows an embodiment which includes a retractable ultrasound reflector in order to operate as an absorption microscope in a pulse reflection mode.

This invention has so far been discussed in relation to pulse echo visualization technique. While pulse echo scanning provides ultrasonic in vivo scanning without the need for any reflecting surface, there are added advantages to be gained in sensitivity by utilizing pulse reflection techniques. In FIG. 7, an embodiment is shown which includes a retractable ultrasound reflector in order to operate as an absorption microscope in a pulse reflection mode. Needle 410 is shown housing the sapphire 415 coupler and attached transducer 414. Sector scanning may be accomplished by any of the methods so far discussed, but which have not been shown in FIG. 7 for purpose of simplicity of illustration of the pulse reflection apparatus. Rod 440 which can be rotated within needle 410 has an attached arm 41 in guide 44 through pin 43. Element 42 provides an acoustic reflection surface. Since reflector 42 is very thin and sharp pointed (wedge point) the shape of 42 is distorted back into guide 44 when reflector 42 is retracted, while being extended it assumes its natural shape to provide an acoustic reflecting surface normal for the ultrasonic beam 60. Reflector 42 is a highly polished metal blade or alternatively may be constructed from polished quartz.

The present invention produces an acoustic image from which a considerable amount of valuable information can be obtained. For instance, by studying cellular structure and tissue architecture and organization in situ it can be determined whether or not removal of the suspected tissue is indicated, therefore a definite diagnosis can be made prior to any surgery or biopsial removal of tissue. Thus unnecessary surgery and removal of tissue with its attendant hazards to the patient may be avoided.

While there have been described above the principles of this invention with specific apparatus and techniques it is to be clearly understood that this description is made only by way of example and not as limitation to the scope of the invention.

What is claimed is:

1. An ultrasound visualization system comprising:
   (a) a needle, said needle having a sharp point at one end and being adapted for insertion into the human body;
   (b) high frequency ultrasound transducer means for producing and receiving acoustical beams of at least 100 MHz frequency from within said needle;
   (c) beam directing means for directing acoustical beams produced by said transducer means radially from said needle at a point outside of said needle;
   (d) scan means coupled to said transducer means for scanning acoustical beams produced by said high frequency ultrasound transducer and directed by said beam directing means; and
   (e) visualization circuitry means for translating acoustical beams received by said transducer means into a visual display.

2. The ultrasound visualization system of claim 1 in which said scan means includes axial scan means for mechanically scanning in an axial direction with respect to said needle, and rotational scan means for mechanically scanning rotationally with respect to said needle.

3. The ultrasound visualization system of claim 2 additionally including means for locating the position of said needle within a human body, said means including a low frequency ultrasound system.

4. The ultrasound visualization system of claim 3 in which said coupling medium is sapphire.

5. The ultrasound visualization system of claim 1 in which said scan means includes electronic scan means for measuring acoustical reflections at various depths by differentiating the time delay of received acoustical beams after an acoustical beam has been produced.

6. The ultrasound visualization system of claim 1 additionally including means for locating the position of said needle within a human body, said means including a low frequency ultrasound system.

7. The ultrasound visualization system of claim 1 in which said needle has a cylindrical surface and defines an aperture in its cylindrical surface and in which said high frequency ultrasound transducer and acoustical beam directing means includes:
   (A) a transducer positioned within said needle to produce and receive acoustical beams axially within said needle;
   (B) a coupling medium position within said needle and adjacent to said transducer, said coupling medium having acoustical properties such that an acoustical beam travels in a straight line within said medium;
   (C) a reflector defining a reflective surface which is positioned within said needle at approximately a 45° angle to the central axis of said needle, and adjacent to said coupling medium, whereby an acoustical beam axially traveling within said coupling medium is reflected by said reflective surface to travel radially within said needle and in said coupling medium toward the aperture in said needle; and
   (D) concave lens means positioned at the aperture in said needle for focusing an axial beam traveling radially within said needle to a point outside of said needle.

8. The ultrasound visualization system of claim 7 additionally including material having tissuelike accoustical properties attached to the concavity of said lens means, said tissuelike material having an outside convex surface matching the cylindrical surface of said needle to reduce induced tissue motion effects.

9. The ultrasound visualization system of claim 8 in which said material having tissue-like acoustical properties is plastisol.

10. The ultrasound visualization system of claim 7 in which said high frequency ultrasound transducer means includes means for producing and receiving acoustical beams of at least 400 MHz frequency.

11. The ultrasound visualization system of claim 10 additionally including material having tissue-like accoustical properties attached to the concavity of said lens means, said tissuelike material having an outside convex surface matching the cylindrical surface of said needle to reduce induced tissue motion effects.

12. The ultrasound visualization system of claim 11 in which said material having tissue-like acoustical properties is plastisol.

13. The ultrasound visualization system of claim 7 in which said high frequency ultrasound transducer means includes means for producing and receiving acoustical beams of at least 500 MHz frequency.

14. The ultrasound visualization system of claim 13 additionally including material having tissue-like accoustical properties attached to the concavity of said lens means, said tissuelike material having an outside convex surface matching the cylindrical surface of said needle to reduce induced tissue motion effects.

15. The ultrasound visualization system of claim 1 additionally including a reflector and means for projecting said reflector from said needle, said reflector defining an ultrasonically reflective surface which, when projected by said projecting means, reflects beams directed from said needle by said beam directing means back towards said needle.

16. The ultrasound visualization system of claim 15 in which said means for projecting a retractable ultrasonic reflecting surface includes a polished metal wedge having a reflecting surface which is normal to an ultrasonic beam directed from said needle, said wedge being mounted to a retracting member, said retracting member being movable to retract said wedge into a groove within said needle.

17. The ultrasonic visualization system of claim 1 in which said high frequency ultrasound transducer means includes means for producing and receiving acoustical beams of at least 400 MHz frequency.

18. The ultrasound visualization system of claim 17 additionally including means for locating the position of said needle within a human body, said means including a low frequency ultrasound system.

19. The ultrasound visualization system of claim 1 in which said high frequency ultrasound transducer means includes means for producing and receiving acoustical beams of at least 500 MHz frequency.

20. The ultrasound visualization system of claim 19 additionally including a reflector and means for projecting said reflector from said needle, said reflector defining an ultrasonically reflective surface which, when projected by said projecting means, reflects beams directed from said needle by said beam directing means back towards said needle.

* * * * *